United States Patent [19]

Shigeyasu et al.

[11] 4,160,108

[45] Jul. 3, 1979

[54] PROCESS FOR PRODUCING TEREPHTHALIC ACID

[75] Inventors: Motoo Shigeyasu; Nobuo Kusano, both of Matsuyama, Japan

[73] Assignee: Matsuyama Petrochemicals Inc., Osaka, Japan

[21] Appl. No.: 770,145

[22] Filed: Feb. 18, 1977

[30] Foreign Application Priority Data

Feb. 24, 1976 [JP] Japan .................................. 51/18421

[51] Int. Cl.$^2$ ............................................. C07C 51/33
[52] U.S. Cl. ..................................................... 562/416
[58] Field of Search ...................... 260/524 R; 562/416

[56] References Cited

U.S. PATENT DOCUMENTS 3,846,487  11/1974  Shigeyasu ............................ 260/524
3,920,735  11/1975  Wampfler ............................. 260/524

Primary Examiner—A. Siegel
Attorney, Agent, or Firm—Sughrue, Rothwell, Mion, Zinn and Macpeak

[57] ABSTRACT

In a process for producing terephthalic acid which comprises subjecting p-xylene to a liquid-phase oxidation in a lower aliphatic carboxylic acid solvent in the presence of a cobalt compound-manganese compound-bromine or bromine compound catalyst and molecular oxygen, the improvement which comprises
the % by weight based on the weight of said lower aliphatic carboxylic acid solvent of the cobalt component (as cobalt) in the catalyst being within the range of $$-6.00 \times 10^{-4} t + 1.65 \times 10^{-1} \text{ to } -2.50 \times 10^{-3} t + 6.25 \times 10^{-1}$$

wherein t is the reaction temperature in °C.;
the weight ratio of the manganese component (as manganese) in the catalyst to the cobalt component in the catalyst ranges from 0.25:1 to 1:1 and also the amount of the manganese component in the catalyst is 0.05% by weight or less based on the weight of said lower aliphatic carboxylic acid solvent; and
the % by weight based on the weight of said lower aliphatic carboxylic acid solvent of the bromine component (as atomic bromine) in the catalyst is within the range of $$-4.40 \times 10^{-4} t + 1.08 \text{ to } -1.00 \times 10^{-3} t + 2.50$$

wherein t is as defined above.

14 Claims, 2 Drawing Figures

PROCESS FOR PRODUCING TEREPHTHALIC ACID

BACKGROUND OF THE INVENTION

1. Field of the Invention

The present invention relates to a process for producing terephthalic acid. More particularly, the invention relates to a process for producing high purity terephthalic acid suitable for use as starting materials to obtain a high quality polyester by direct polymerization with glycols.

2. Description of the Prior Art

A so-called "direct polymerization process" in which terephthalic acid is directly reacted with glycols (e.g., as described in U.S. Pat. Nos. 3,451,910 and 3,406,153) is an improvement over the complicated process for producing polyethylene terephthalate by subjecting terephthalic acid to an esterification to obtain dimethyl terephthalate and then conducting an ester exchange reaction with glycols and a polycondensation reaction (e.g., as described in U.S. Pat. Nos. 2,647,885 and 2,578,660). In the direct polymerization process the terephthalic acid used must have a very high purity.

Therefore, the terephthalic acid obtained by oxidizing an alkylated aromatic hydrocarbon with molecular oxygen in the presence of a catalyst comprising a heavy metal compound and a bromine compound (or bromine) using a lower aliphatic carboxylic acid as a solvent, which was developed by Scientific Design Co. (and is known as the "SD process") and is industrially widely employed as described in the specification of Japanese Patent Publication No. 2666/1956 (corresponding to the original specification of a continuation-in-part application, U.S. Pat. No. 2,833,816) contains reaction intermediate products such as 4-carboxybenzaldehyde, p-toluic acid, etc. and reaction by-products having an undetermined indefinite structure in a large amount and cannot be used in a direct polymerization without purification. Hence, it is necessary to purify terephthalic acid obtained by the SD process to achieve a high purity using various purification techniques which are complicated and uneconomical. It would be most advantageous if high purity terephthalic acid could be obtained directly by a liquid-phase oxidation of an aromatic hydrocarbon such as p-xylene, in a single step.

In a liquid-phase oxidation reaction for producing terephthalic acid, various methods of improving the activity of the catalyst by limiting the ratio of the heavy metal component and the bromine component which are used for the catalyst, the concentration thereof, etc. to a preferred range have been heretofore proposed as described, for example, in Japanese Patent Publications 15531/1967, 329/1970, etc., but these methods can be characterized as employing as reaction conditions relatively mild conditions of atmospheric pressure and low temperature (in general, around the boiling point of reaction solution, and where acetic acid is used as the solvent, about 118° C.). Where an oxidation reaction is conducted under such mild reaction conditions there is the disadvantage that the reaction rate is markedly reduced and, as a result, to obtain a yield the same as that obtained in the process using conventional high temperature and pressure conditions the intent is to limit the ratio (amount) of catalyst used and the concentration thereof to a specific range thereby to increase the reaction rate. However, terephthalic acid of satisfactory purity and color for use in the direct polymerization is not obtained.

SUMMARY OF THE INVENTION

An object of the present invention is to provide a process for producing high purity terephthalic acid.

Another object of the present invention is to provide a process for producing terephthalic acid having high purity and good color using a direct liquid-phase oxidation of p-xylene in a single step.

As a result of extensive investigations in detail with respect to a heavy metal-bromine system oxidation catalyst used in the conventional liquid-phase oxidation as described, for example, in Japanese Patent Publication 2666/1959 (as described before), it has now been found that high purity terephthalic acid can be obtained advantageously from an industrial standpoint by employing a process where the amount of the heavy metal component and the bromine component used is limited to a specific range in specific temperature ranges.

Accordingly, the present invention provides a process for producing terephthalic acid by subjecting p-xylene to a liquid-phase oxidation in the presence of a cobalt compound-manganese compound-bromine (or a bromine compound) catalyst and molecular oxygen in a lower aliphatic carboxylic acid as a solvent, where the reaction is conducted such that the amount of the cobalt component in the catalyst is $-6.00 \times 10^{-4}t + 1.65 \times 10^{-1}$ to $-2.50 \times 10^{-3}t + 6.25 \times 10^{-1}\%$ by weight based on the weight of the lower aliphatic carboxylic acid solvent, wherein $t$ is the reaction temperature in degrees centigrade (hereinafter the same), the weight ratio of the manganese component in the catalyst to the cobalt component in the catalyst is 0.25:1 to 1:1 and also the amount of the manganese component is 0.05% by weight or less based on the weight of the lower aliphatic carboxylic acid solvent, and the amount of the bromine component in the catalyst is $-4.40 \times 10^{-3}t + 1.08$ to $-1.00 \times 10^{-2}t + 2.50\%$ by weight based on the weight of the lower aliphatic carboxylic acid solvent. In the above, the amount of the cobalt component in the catalyst is calculated as cobalt metal. The same calculation is made to manganese and atomic bromine.

According to the process of the present invention as described above, terephthalic acid having good purity and color can be obtained in a high yield.

BRIEF DESCRIPTION OF THE ACCOMPANYING DRAWINGS

DETAILED DESCRIPTION OF THE INVENTION

Figure 2:
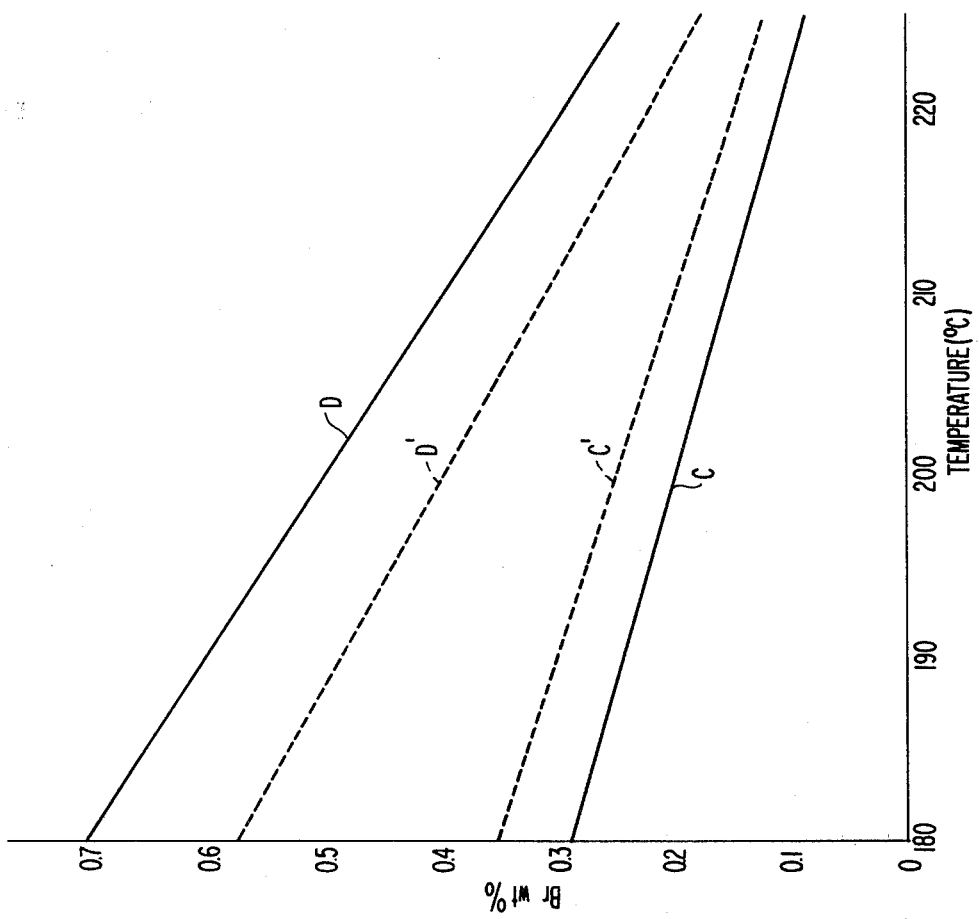
FIG. 2 is a graph showing the relationship between the amount of the bromine component and the temperature of the solvent.

The p-xylene used in the present invention can be that conventionally used in the production of terephthalic acid. Preferably the p-xylene has a purity of about 98% by weight or more, but p-xylene produced in a conventional manner can be used in the present invention.

Lower aliphatic carboxylic acids which are conventionally used in the process for producing terephthalic acid using a liquid-phase oxidation of p-xylene can be used as solvents in the process of the present invention. In general, a saturated aliphatic acid having 1 to 8 carbon atoms, preferably 2 to 4 carbon atoms, is preferred. For example, acetic acid, propionic acid, n-butyric acid or the like can in general be well used. Specifically, from the standpoint of the quality of the product when the solvent decomposes during reaction, the influence in recovery of the solvent, the cost of the solvent, etc., an acid having a lesser number of carbon atoms is preferred and, of those, acetic acid is the most preferred.

Examples of suitable cobalt compounds and manganese compounds which can be used in the process of the present invention include cobalt bromide and manganese bromide (generally, used in a form of hydrate of these bromides) which are capable of simultaneously providing the bromine component, a cobalt or manganese salt of an aliphatic carboxylic acid (generally, used in a form of a hydrate of these salts), etc. Examples of suitable salts of aliphatic carboxylic acids are those of aliphatic carboxylic acids having 2 to 4 carbon atoms and include salts of acetic acid, salts of propionic acid, salts of butyric acid or the like. A salt having 5 or more carbon atoms results in deterioration of the quality of terephthalic acid. Further, examples of a cobalt compound and a manganese compound which can be used in the process of the present invention include cobalt or manganese salts of naphthenic acid having 7 to 15 carbon atoms; cobalt or manganese salts of aromatic acids such as terephthalic acid, benzoic acid or the like; a complex such as acetylacetonates of cobalt or mangenese; metal powders of cobalt or manganese; etc. Bromides and salts of acetic acid are particularly preferred.

Examples of bromine components used as a catalyst include hydrobromic acid (commercially available 48% by weight hydrobromic acid can be directly used), manganese bromide, cobalt bromide, bromine, bromoform, tetrabromoethane, monobromoacetic acid, dibromoacetic acid, tribromoacetic acid, α, α, α', α'-tetrabromo-p-xylene or the like. Where an alkali metal compound such as sodium bromide, potassium bromide, etc. is used in an amount corresponding to the necessary amount of the component contained therein, the amount of the alkali metal becomes large whereby the quality of terephathalic acid deteriorates, but terephthalic acid having high quality (specifically, a good color) can be obtained in the presence of a slight amount of alkali metal, i.e., up to about 200 ppm based on the weight of a solvent used. Therefore, a mixture of a bromine compound containing an alkali metal with a bromine compound which does not contain an alkali metal or with bromine can be used as the bromine component.

The above-described compounds can be used in admixture or in any combination thereof as the catalyst.

Figure 1:
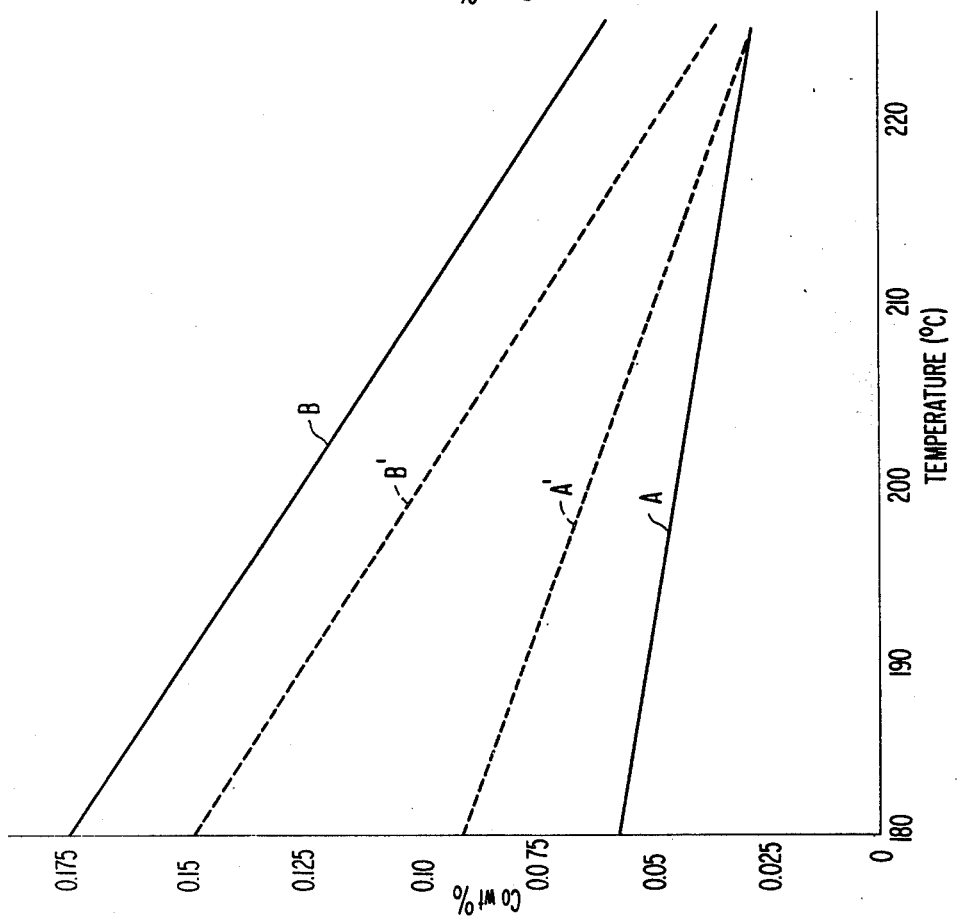
FIG. 1 is a graph showing the relationship between the amount of the cobalt component and the temperature of the solvent.

As described above, the amount of the cobalt compound used is such that the amount of the cobalt component is $-6.00\times10^{-4}t+1.65\times10^{-1}$ to $-2.50\times10^{-3}t+6.25\times10^{-1}\%$ by weight based on the weight of the lower aliphatic carboxylic acid solvent and is the area defined by lines A and B in FIG. 1. The preferred amount of the cobalt component is $-1.33\times10^{-3}t+3.30\times10^{-1}$ to $-2.50\times10^{-3}t+6.00\times10^{-1}\%$ by weight based on the weight of the solvent and is the area defined by lines A' and B' in FIG. 1.

If the amount of the cobalt component used is smaller than $-6.00\times10^{-4}t+1.65\times10^{-1}\%$ by weight, terephthalic acid having high purity and good color cannot be obtained. Further, if the amount of the cobalt component is larger than $-2.50\times10^{-3}t+6.25\times10^{-1}\%$ by weight, though the reason is unknown whether since the amount of cobalt compound is too large, it is difficult for the manganese compound to completely dissolve therein, or the manganese salt is oxidized by oxygen to form a solvent-insoluble material, the color of terephthalic acid becomes turbid optionally depending upon the reaction temperature and pure white terephthalic acid sometimes cannot be obtained. Additionally, a large amount carbon dioxide gas is generated by decomposition of the lower aliphatic carboxylic acid as the solvent, it is not advantageous from an economical standpoint.

The manganese compound must be used in an amount satisfying both requirements that (1) the weight ratio of the manganese component to the cobalt component in the catalyst is 0.25:1 to 1:1 and (2) the amount of the manganese component is also 0.05% by weight or less based on the weight of the lower aliphatic carboxylic acid solvent. The preferred weight ratio of the amount of the manganese component to the amount of the cobalt component is 0.4:1 to 0.7:1 and 0.02 to 0.04% by weight based on the weight of the lower aliphatic carboxylic acid solvent respectively. If the amount of the manganese component is below a ratio of 0.25:1 the weight of the cobalt component, terephthalic acid having good purity cannot be obtained. On the other hand, if the amount of the manganese component used is above a ratio of 1:1 the weight of the cobalt component, the purity of the terephthalic acid is degraded somewhat and a situation where the color is not pure-white occurs. Further, since a large amount of carbon dioxide gas is generated by decomposition of the lower aliphatic carboxylic acid solvent, it is not advantageous from an economical standpoint. Furthermore, the weight ratio of the manganese component to the cobalt component, i.e. 0.25:1 to 1:1 times by weight, is a necessary element but is not the only sufficient element. That is, the amount of manganese component used must satisfy the requirement of 0.05% by weight or less based on the weight of the lower aliphatic carboxylic acid solvent. Because, even though the amount of manganese component is within the weight ratio of 0.25:1 to 1:1 the weight of the cobalt component, if the amount thereof exceeds 0.05% by weight based on the weight of the lower aliphatic carboxylic acid solvent, although the reason is unknown whether the manganese compound is difficult to dissolve in a solvent completely or the manganese component is oxidized with oxygen to form a solvent-insoluble material, pure-white terephthalic acid cannot be obtained optionally depending upon the reaction temperature. Further, since the decomposition of the lower aliphatic carboxylic acid solvent becomes large, this is disadvantageous.

Bromine or the bromine compound used in the process of the present invention must be present in an amount such that the amount of bromine component is $-4.40\times10^{-3}t+1.08$ to $-1.00\times10^{-2}t+2.50\%$ by weight based on the weight of the lower aliphatic carboxylic acid solvent. This amount corresponds to the area defined by lines C and D in FIG. 2. The preferred amount of bromine or the bromine component is $-5.00\times10^{-3}t+1.25$ to $-8.75\times10^{-3}t+2.15\%$ by weight based on the weight of the lower aliphatic carboxylic acid solvent and corresponds to the area defined by lines C' and D' in FIG. 2. If the amount of bromine or bromine component used is below $-4.40 \times 10^{-3}t + 1.08\%$ by weight based on the weight of the lower aliphatic carboxylic acid solvent, terephthalic acid having good purity cannot be obtained. On the other hand, if the amount of bromine or the bromine component used is above $-1.00 \times 10^{-2}t + 2.50\%$ by weight based on the weight of the lower aliphatic carboxylic acid solvent, terephthalic acid having good color cannot be obtained. The preferred amount of the bromine component is more than 0.2% by weight based on the weight of the lower aliphatic carboxylic acid solvent.

The catalyst is used by dissolving the catalyst into the reaction solvent in the process of the present invention.

The oxidation reaction in the process of the present invention is conducted in the presence of molecular oxygen (i.e., oxygen gas or an oxygen containing gas). The oxidation reaction is conducted by feeding oxygen gas or a mixed gas containing oxygen gas into the reaction solution. Any inert gas can be used as a gas in admixture with oxygen gas. Examples of suitable inert gases include nitrogen, helium, neon, argon or the like. From a practical standpoint, a mixed gas of oxygen gas and nitrogen gas, i.e., air, is used. The amount (concentration) of oxygen in a mixed gas is at least about 10% by volume based on the total volume of the mixed gas, but if the oxygen concentration in the exhaust gas is too high, there is the danger of explosion. Therefore, the content of oxygen gas and the feeding rate are generally determined so that the oxygen concentration in the exhaust gas is not larger than about 8%, preferably 6%, by volume based on the volume of the exhaust gas. Where an oxygen-containing gas is fed under conditions such that the amount of oxygen in the exhaust gas is too low, terephthalic acid having good quality cannot be obtained. Therefore, the content of oxygen in the gas and the feeding rate of the oxygen-containing gas are generally determined so as to be not smaller than about 3%, preferably 4%, by volume based on the volume of the exhaust gas. The exhaust gas after the oxidation reaction can be mixed with oxygen to adjust the concentration for re-use if desired. The feeding rate is necessary to an extent that no clogging of the feed pipes occurs and, in the case of using air, is generally 2 to 8 liters per g of p-xylene per minute, preferably 4 to 5 liters per g of p-xylene per minute.

In general, p-xylene is fed into a reaction vessel under pressure using a pump without specifically heating. At this time, it is preferred for the p-xylene to be fed as a mixed solution with the lower aliphatic carboxylic acid solvent, but it is possible to feed p-xylene and the lower aliphatic carboxylic acid solvent separately.

The amount of solvent in a reaction solution is preferably about 2 or more times the weight of the p-xylene. If the amount of solvent is below about 2 times the weight of the p-xylene, the quality of the terephthalic acid tends to be deteriorated. In general, a suitable amount of the solvent is 3 to 6 times the weight of the p-xylene. If the amount is above 6 times the weight of the p-xylene, due to the small amount of p-xylene charged, the quality of the terephthalic acid is further improved but the output of the product is decreased and it is disadvantageous from an economical standpoint.

The oxidation reaction is generally conducted at a temperature of from about 180° to about 225° C. From an economical standpoint, i.e., production rate per unit time, a temperature of 195° C. or more is preferred. However, disregarding economics, even if the temperature is reduced to about 180° C., high quality terephthalic acid can be obtained by increasing the amount of the solvent used. When the amount of solvent is about 3 times the weight of p-xylene, a temperature of 195° to 225° C. is suitable, and when the amount of solvent is about 6 times the weight of p-xylene, high quality terephthalic acid can be obtained even at a temperature of about 180° C. If the reaction temperature is above 225° C., the color of terephthalic acid obtained tends to become poor and from the fact that a large amount of carbon dioxide gas is generated by decomposition of the lower aliphatic carboxylic acid solvent, such a higher temperature is disadvantageous from an economical standpoint. The most preferred temperature range is 195° to 215° C.

The reaction pressure preferably is above the vapor pressure of reaction solution at the reaction temperature. Where acetic acid is used as a solvent, a pressure of about 8 kg/cm² or more is preferred at a reaction temperature of 200° C. In general, it is preferred for the pressure to be high since the oxygen partial pressure becomes high and the solubility of oxygen gas increases, but since increased pressure requires pressure-resistant reaction vessels, compressors for pressurization, etc., the pressure is generally about 100 kg/cm² or less, preferably 15 to 30 kg/cm².

The reaction time will vary depending upon the reaction temperature, the amount of catalyst, etc., but such is generally determined by conditions so that the reaction is completed within about 4 hours.

The amount of water in the reaction system is controlled so as to be about 15% by weight or less based on the weight of the reaction solution by controlling amount of water in materials supplied to the reaction system, removal of water produced during the reaction, or the like.

In the present invention, in addition to the above-described catalysts, aliphatic aldehydes (generally aldehydes having 1 to 4 carbon atoms, e.g., acetaldehyde), aliphatic ketones (generally ketones having 3 to 5 carbon atoms, e.g., methyl ethyl ketone), aliphatic alcohols (generally alcohols having 1 to 4 carbon atoms, e.g., ethyl alcohol; but tert-butyl alcohol is not preferred), etc., can be used as a reaction accelerator. The accelerator causes the reaction to proceed smoothly and to further reduce the formation of impurities where the amount of the bromine component is relatively small. The amount of these accelerators added is generally about 0.5 to about 10% by weight based on the weight of the solvent.

Further, as a promotor, a bromide of lanthanum, cerium, praseodyminum, neodymium, samarium, europium, gadolinium, terbium, dysprosium, holmium, erbium, thulium, ytterbium, lutecium, uranium, nickel, chromium and rubidium; an aliphatic carboxylic acid salt of the above described metals such as an acetic acid salt of the above described metals, a propionic acid salt of the above described metals, an n-butyric acid salt of the above described metals, etc., may be added, but such is not essential. Further, it is possible to use as a promotor the above-described metal salts of naphthenic acid having 7 to 15 carbon atoms; cobalt or manganese salts of aromatic acids such as terephthalic acid, benzoic acid or the like; a complex such as an acetylacetonate of cobalt or manganese; metal powders of cobalt or manganese; etc., but such use is not essential. The amount of the above compounds, calculated as elemental metal, added is generally 0.1 to 10 wt% based on the weight of cobalt.

After completion of reaction the reaction products are separated from the liquid-phase using a solid-liquid separator, such as a centrifugal separator, a decanter or the like, washed with a solvent (e.g., that used as a reaction solvent with acetic acid being preferred) and dried to obtain solid terephthalic acid.

The present invention is illustrated in greater detail by reference to the following Examples. However, the present invention is not to be construed as being limited to these Examples only. Unless otherwise indicated, all parts, percents, ratios and the like are by weight.

EXAMPLE 1

Into a 40 liter pressure resistant reaction vessel of titanium equipped with a reflux condenser, a stirrer, a heating means, an inlet for raw materials, a gas inlet and an outlet for the reaction products were charged 12 Kg of acetic acid, 25.4 g of cobalt acetate tetrahydrate, 26.8 g of manganese acetate tetrahydrate and 50.6 of a 48% hydrobromic acid aqueous solution (the amount of the cobalt component based on the acetic acid was 0.05% by weight, the amount of the manganese component based on the acetic acid was 0.05% by weight (i.e., the weight ratio of the manganese component to the cobalt component was 1:1) and the amount of the bromine component based on the acetic acid was 0.20% by weight), and 1.5 Kg/hr of p-xylene and air at the rate of 5 liters per gram of p-xylene were fed into the system for 2 hours to conduct the oxidation reaction at a temperature of 210° C. and at a pressure of 25 Kg/cm$^2$. After the reaction was completed, the reaction product was withdrawn. The solid product was separated from the liquid phase, washed with acetic acid and dried. The properties and the yield of the terephthalic acid obtained are shown in Table 1 below.

EXAMPLE 2

The same procedure as in Example 1 was followed except that 50.8 g of cobalt acetate tetrahydrate, 26.8 g of manganese acetate tetrahydrate and 50.6 g of a 48% hydrobromic acid aqueous solution were used as the heavy metal catalyst (the amount of the cobalt component based on the acetic acid was 0.10% by weight, the amount of the manganese component based on the acetic acid was 0.05% by weight (i.e., the weight ratio of the manganese component to the cobalt component was 0.5:1) and the amount of the bromine component based on the acetic acid was 0.20% by weight)). The properties and the yield of the terephthalic acid obtained are shown in Table 1 below.

COMPARATIVE EXAMPLE 1

The same procedure as in Example 1 was followed except that 15.2 g of cobalt acetate tetrahydrate, 26.8 g of manganese acetate tetrahydrate and 50.6 g of a 48% hydrobromic acid aqueous solution were used (the amount of the cobalt component based on the acetic acid was 0.03% by weight, the amount of the manganese component based on the acetic acid was 0.05% by weight (i.e., the weight ratio of the manganese component to the cobalt component was 1.7:1) and the amount of the bromine component based on the acetic acid was 0.20% by weight)). The properties and the yield of the terephthalic acid obtained are shown in Table 1 below.

COMPARATIVE EXAMPLE 2

The same procedure as in Example 1 was followed except that 101.5 g of cobalt acetate tetrahydrate, 26.8 g of manganese acetate tetrahydrate and 50.6 g of a 48% hydrobromic acid aqueous solution were used (the amount of the cobalt component based on the acetic acid was 0.20% by weight and the amount of the manganese component based on the acetic acid was 0.05% by weight (i.e., the weight ratio of the manganese component to the cobalt component was 0.25:1) and the amount of the bromine component to the acetic acid was 0.20% by weight). The properties and the yield of the terephthalic acid obtained are shown in Table 1 below.

EXAMPLE 3

The same procedure as in Example 1 was followed except that 25.4 g of cobalt acetate tetrahydrate and 50.6 g of a 48% hydrobromic acid aqueous solution were used (the amount of the cobalt component based on the acetic acid was 0.05% by weight and the amount of the bromine component based on the acetic acid was 0.20% by weight) and 13.4 g of manganese acetate tetrahydrate was used so that the amount of the manganese component based on the acetic acid was 0.025% by weight (i.e., the weight ratio of the manganese component to the cobalt component was 0.5:1). The properties and the yield of the terephthalic acid obtained are shown in Table 1 below.

COMPARATIVE EXAMPLES 3-4

The same procedures as in Example 1 were followed except that 25.4 g of cobalt acetate tetrahydrate and 50.6 g of a 48% hydrobromic acid aqueous solution were used (the amount of the cobalt component based on the acetic acid was 0.05% by weight and the amount of the bromine component based on the acetic acid was 0.20% by weight) and 5.4 g and 53.6 g of manganese acetate tetrahydrate were used so that the amount of the manganese component based on the acetic acid was 0.01% and 0.10% by weight, respectively (i.e., the weight ratio of the manganese component to the cobalt component was 0.2:1 and 2.0:1 respectively). The properties and the yield of the terephthalic acid obtained are shown in Table 1 below.

COMPARATIVE EXAMPLE 5

The same procedure as in Example 1 was followed except that 50.8 g of cobalt acetate tetrahydrate, 40.2 g of manganese acetate tetrahydrate and 50.6 g of a 48% hydrobromic acid aqueous solution were used (the amount of the cobalt component based on the acetic acid was 0.10% by weight and the amount of manganese component based on the acetic acid was 0.075% by weight (i.e., the weight ratio of the manganese component to cobalt component was 0.75:1) and the amount of the bromine component based on the acetic acid was 0.20% by weight). The properties and the yield of the terephthalic acid obtained are shown in Table 1 below.

EXAMPLE 4

The same procedure as in Example 1 was followed except that 25.4 g of cobalt acetate tetrahydrate and 13.4 g of manganese acetate tetrahydrate were used (the amount of cobalt component based on the acetic acid was 0.05% by weight and the amount of the manganese component based on the acetic acid was 0.025% by weight (i.e., the weight ratio of the manganese component to the cobalt component was 0.5:1)) and 88.6 g of a 48% hydrobromic acid aqueous solution was used so that the amount of the bromine component based on the acetic acid was 0.35% by weight. The properties and the yield of the terephthalic acid obtained are shown in Table 1 below.

EXAMPLE 5

The same procedure as in Example 1 was followed except that 466 g of cobalt bromide hexahydrate and 18.8 g of manganese acetate tetrahydrate were used (the amount of the cobalt component based on the acetic acid was 0.07% by weight and the amount of the manganese component based on the acetic acid was 0.035% by weight (i.e., the weight ratio of the manganese component to the cobalt component was 0.5:1) and the amount of the bromine component based on the acetic acid was 0.19% by weight). The properties and the yield of the terephthalic acid obtained are shown in Table 1 below.

COMPARATIVE EXAMPLES 6-7

The same procedures as in Example 1 were followed except that 25.4 g of cobalt acetate tetrahydrate and 13.4 g of manganese acetate tetrahydrate were used (the amount of the cobalt component based on the acetic acid was 0.05% by weight and the amount of the manganese component based on the acetic acid was 0.025% by weight (i.e., the weight ratio of the manganese component to the cobalt component was 0.5:1)), and 25.3 g and 126.6 g of a 48% hydrobromic acid aqueous solution were used so that the amount of the bromine component based on the acetic acid was 0.10% by weight and 0.50% by weight, respectively. The properties and the yield of the terephthalic acid obtained are shown in Table 1 below.

EXAMPLES 6-8

The same procedures as in Example 1 were followed except that 30.5 g of cobalt acetate tetrahydrate, 16.1 g of manganese acetate tetrahydrate and 57.0 g of a 48% hydrobromic acid aqueous solution were used (the amount of the cobalt component based on the acetic acid was 0.06% by weight, the amount of the manganese component based on the acetic acid was 0.03% by weight (i.e., the weight ratio of the manganese component to the cobalt component was 0.5:1) and the amount of the bromine component based on the acetic acid was 0.225% by weight) and the reaction temperature was 200° C. (Example 6), 210° C. (Example 7) and 220° C. (Example 8). The properties and the yield of the terephthalic acid obtained are shown in Table 1 below.

EXAMPLE 9

The same procedure as in Example 1 was followed except that 40.6 g of cobalt acetate tetrahydrate, 21.5 g of manganese acetate tetrahydrate and 88.6 g of a 48% hydrobromic acid aqueous solution were used (the amount of the cobalt component based on the acetic acid was 0.08% by weight, the amount of the manganese component based on the acetic acid was 0.04% by weight (i.e., the weight ratio of the manganese component to the cobalt component was 0.5:1) and the amount of the bromine component based on the acetic acid was 0.35% by weight), the amount of p-xylene fed was 1.0 Kg/hr and the reaction temperature was 190° C. The properties and the yield of the terephthalic acid obtained are shown in Table 1 below.

COMPARATIVE EXAMPLE 8

The same procedure in Example 1 was followed except that the reaction temperature was 230° C. The properties and the yield of the terephthalic acid obtained are shown in Table 1 below.

EXAMPLE 10

The same procedure as in Example 1 was followed except that 26.4 g of cobalt propionate was used instead of 25.4 g of cobalt acetate (the amount of the cobalt component based on the acetic acid was 0.05% by weight). The properties and the yield of the terephthalic acid obtained are shown in Table 1.

EXAMPLE 11

The same procedure as in Example 1 was followed except that 29.0 g of manganese n-butyrate was used instead of 26.8 g of manganese acetate (the amount of the manganese component based on the acetic acid was 0.05% by weight, i.e., the weight ratio of the manganese component to the cobalt component was 1:1). The properties and the yield of the terephthalic acid obtained are shown in Table 1 below.

EXAMPLE 12

The same procedure as in Example 1 was followed except that 26.0 g of tetrabromoethane was used instead of 50.6 g of a 48% hydrobromic acid aqueous solution (the amount of the bromine component based on the acetic acid was 0.20% by weight). The properties and the yield of the terephthalic acid obtained are shown in Table 1 below.

EXAMPLE 13

The same procedure as in Example 1 was followed except that 12 Kg of propionic acid was used instead of 12 Kg of acetic acid. The properties and the yield of the terephthalic acid obtained are shown in Table 1 below.

EXAMPLE 14

The same procedure as in Example 1 was followed except that 7 l/min. of a mixed gas containing oxygen in a concentration of 15% by volume per gram of p-xylene was used instead of 5 liters of air. The properties and the yield of the terephthalic acid obtained are shown in Table 1 below.

Table 1

| Example No. | Reaction Product Yield and Characteristics | | | | | |
|---|---|---|---|---|---|---|
| | (A) | (B) | (C) | (D) | (E) | (F) |
| Example 1 | 99.98 | 170 | 0.01 | 0.2 | 97 | 13 |
| Example 2 | " | 150 | 0.01 | 0.3 | 97 | 19 |
| Comparative Example 1 | 99.94 | 510 | 0.01 | 0.7 | 96 | 10 |
| Example 2 | 99.98 | 150 | 0.08 | 2.9 | 97 | 32 |
| Example 3 | 99.98 | 160 | 0.01 | 0.2 | 97 | 10 |
| Comparative Example 3 | 99.95 | 380 | 0.01 | 0.2 | 96 | 8 |
| Example 4 | 99.97 | 260 | 0.07 | 2.1 | 97 | 19 |
| Example 5 | 99.97 | 240 | 0.06 | 1.8 | 97 | 23 |
| Comparative Example 4 | 99.98 | 150 | 0.01 | 0.4 | 97 | 13 |
| Example 6 | 99.94 | 450 | 0.01 | 0.2 | 96 | 8 |
| Example 7 | 99.98 | 140 | 0.04 | 1.9 | 97 | 15 |
| Example 5 | 99.98 | 150 | 0.01 | 0.2 | 97 | 9 |
| Example 6 | 99.97 | 210 | 0.01 | 0.2 | 97 | 8 |
| Example 7 | 99.98 | 150 | 0.01 | 0.2 | 97 | 12 |
| Example 8 | 99.98 | 110 | 0.01 | 0.5 | 97 | 16 |
| Example 9 | 99.97 | 220 | 0.01 | 0.2 | 97 | 9 |
| Comparative Example 8 | 99.99 | 100 | 0.04 | 1.7 | 97 | 20 |

Table 1-continued

| Example No. | Reaction Product Yield and Characteristics | | | | | |
|---|---|---|---|---|---|---|
| | (A) | (B) | (C) | (D) | (E) | (F) |
| Example 10 | 99.98 | 170 | 0.01 | 0.2 | 97 | 13 |
| Example 11 | 99.98 | 170 | 0.01 | 0.2 | 97 | 13 |
| Example 12 | 99.98 | 170 | 0.01 | 0.2 | 97 | 13 |
| Example 13 | 99.98 | 190 | 0.01 | 0.3 | 97 | 14 |
| Example 14 | 99.97 | 210 | 0.01 | 0.4 | 97 | 10 |

(A) Purity of terephthalic acid in % by weight,
(B) Content of 4-carboxybenzaldehyde in ppm,
(C) Molar extinction coefficient (at 380 mμ). After dissolving 5 g. of terephthalic acid in 100 ml. of 2 N aqueous ammonia the absorption of the solution at 380 mμ was measured by means of a spectrophotometer. The smaller is the value, the better is the color.
(D) Color difference b-value. The so-called external color or appearance which shows the reflected light from solid terephthalic acid measured using a color-difference meter (CM-20) made by the Color Machine Co., the b-value shows yellow (+)-blue(−), and the smaller is the value, the better is the color within the range of the example of this invention.
(E) Theoretical yield of terephthalic acid in mole %, and
(F) Amount of $CO_2$ gas generated in mol/hr.

While the invention has been described in detail and with reference to specific embodiments thereof, it will be apparent to one skilled in the art that various changes and modifications can be made therein without departing from the spirit and scope thereof.

What is claimed is:

1. In a process for producing terephthalic acid which comprises subjecting p-xylene to a liquid-phase oxidation in a lower aliphatic carboxylic acid solvent in the presence of a cobalt compound-manganese compound-bromine or bromine compound catalyst and molecular oxygen, the improvement which comprises
   the % by weight based on the weight of said lower aliphatic carboxylic acid solvent of the cobalt component (as cobalt) in the catalyst being within the range of $$-6.00 \times 10^{-4} t + 1.65 \times 10^{-1} \text{ to } -2.50 \times 10^{-3} t + 6.25 \times 10^{-1}$$

wherein t is the reaction temperature of 180° to 225° C.;
   the weight ratio of the manganese component (as manganese) in the catalyst to the cobalt component in the catalyst ranges from 0.25:1 to 1:1 and also the amount of the manganese component in the catalyst is 0.05% by weight or less based on the weight of said lower aliphatic carboxylic acid solvent; and
   the % by weight based on the weight of said lower aliphatic carboxylic acid solvent of the bromine component (as atomic bromine) in the catalyst is within the range of $$-4.40 \times 10^{-3} t + 1.08 \text{ to } -1.00 \times 10^{-2} t + 2.50$$

wherein t is as defined above.

2. The process as claimed in claim 1, wherein said lower aliphatic carboxylic acid is a saturated aliphatic acid having 1 to 8 carbon atoms.

3. The process as claimed in claim 1, wherein said cobalt compound is cobalt bromide or a cobalt salt of an aliphatic carboxylic acid having 2 to 4 carbon atoms.

4. The process as claimed in claim 1, wherein said manganese compound is manganese bromide or a manganese salt of an aliphatic carboxylic acid having 2 to 4 carbon atoms.

5. The process as claimed in claim 1, wherein said bromine compound is selected from the group consisting of hydrobromic acid, manganese bromide, cobalt bromide, bromoform, tetrabromoethane, monobromoacetic acid, dibromoacetic acid, tribromoacetic acid, 60, $\alpha$, $\alpha'$, $\alpha'$-tetrabromo-p-xylene, sodium bromine and potassium bromide.

6. The process as claimed in claim 1, wherein the reaction pressure is a pressure above the vapor pressure of the reaction solution at the reaction temperature.

7. The process as claimed in claim 1, wherein the amount of said aliphatic carboxylic acid solvent is 2 to 6 times by weight the weight of the p-xylene.

8. The process as claimed in claim 1, wherein the percent by weight based on the weight of lower aliphatic carboxylic acid solvent of the cobalt component (as cobalt) in the catalyst is in the range of $$-1.33 \times 10^{-3} t + 3.30 \times 10^{-1} \text{ to } -2.50 \times 10^{-3} t + 6.00 \times 10^{-1}.$$

9. The process as claimed in claim 1, wherein the weight ratio of the manganese component (as manganese) in the catalyst to the cobalt component catalyst ranges from 0.4:1 to 0.7:1.

10. The process as claimed in claim 9, wherein the amount of the manganese component in the catalyst is 0.02 to 0.04% by weight based on the weight of said lower aliphatic carboxylic acid solvent.

11. The process as claimed in claim 10, wherein the percent by weight based on the weight of said lower aliphatic carboxylic acid solvent of the bromine component (as atomic bromine) in the catalyst is within the range of $$-5.00 \times 10^{-3} t + 1.25 \text{ to } -8.75 \times 10^{-3} t + 2.15.$$

12. The process as claimed in claim 11, wherein the reaction temperature is 195° C. or more.

13. The process as claimed in claim 12, wherein the reaction temperature is 195° to 215° C.

14. The process as claimed in claim 1, wherein said catalyst consists essentially of the cobalt compound-manganese compound-bromine or bromine-compound.

* * * * *